(12) United States Patent
Troendle

(10) Patent No.: US 9,144,432 B2
(45) Date of Patent: Sep. 29, 2015

(54) MEDICAL INSTRUMENT

(75) Inventor: Karlheinz Troendle, Geisingen (DE)

(73) Assignee: TROKAMED GmbH, Geisingen (DE)

( * ) Notice: Subject to any disclaimer, the term of this patent is extended or adjusted under 35 U.S.C. 154(b) by 930 days.

(21) Appl. No.: 13/252,326

(22) Filed: Oct. 4, 2011

(65) Prior Publication Data

US 2012/0083815 A1 Apr. 5, 2012

(30) Foreign Application Priority Data

Oct. 5, 2010 (DE) .......................... 10 2010 037 974

(51) Int. Cl.
*A61B 17/3205* (2006.01)
*A61B 17/32* (2006.01)
*A61B 17/3207* (2006.01)
*A61B 17/00* (2006.01)
*A61B 19/00* (2006.01)

(52) U.S. Cl.
CPC ..... *A61B 17/32002* (2013.01); *A61B 17/32053* (2013.01); *A61B 17/320758* (2013.01); *A61B 2017/0046* (2013.01); *A61B 2017/320024* (2013.01); *A61B 2017/320775* (2013.01); *A61B 2019/4873* (2013.01)

(58) Field of Classification Search
CPC ........... A61B 17/32; A61B 17/320016; A61B 17/32002; A61B 2017/320016; A61B 2017/32002; A61B 2017/320024; A61B 2017/320032; A61B 17/32053
USPC ................... 606/169, 170, 180; 600/562–568
See application file for complete search history.

(56) References Cited

U.S. PATENT DOCUMENTS

| 4,732,154 | A | * | 3/1988 | Shiber .......................... 606/159 |
| 4,815,462 | A | | 3/1989 | Clark |
| 5,569,284 | A | | 10/1996 | Young et al. |
| 5,814,044 | A | | 9/1998 | Hooven |
| 5,817,033 | A | * | 10/1998 | DeSantis et al. .............. 600/562 |
| 6,440,148 | B1 | * | 8/2002 | Shiber .......................... 606/159 |
| 6,527,736 | B1 | | 3/2003 | Attinger et al. |
| 6,783,532 | B2 | | 8/2004 | Steiner et al. |
| 7,981,130 | B2 | | 7/2011 | Seeh |
| 2003/0225344 | A1 | | 12/2003 | Miller |
| 2004/0059342 | A1 | * | 3/2004 | Cherfas et al. ................. 606/106 |
| 2006/0004396 | A1 | * | 1/2006 | Easley et al. .................. 606/169 |
| 2010/0266227 | A1 | * | 10/2010 | Higuchi et al. ............... 384/129 |

FOREIGN PATENT DOCUMENTS

| DE | 19859217 | | 7/2000 |
| DE | 10300127 | | 7/2004 |
| DE | 10358279 | | 7/2005 |
| DE | 102007008751 | | 8/2008 |
| EP | 0858774 | A2 | 8/1998 |
| EP | 1201210 | | 5/2002 |
| WO | 2005020826 | | 3/2005 |
| WO | 2005060842 | A1 | 7/2005 |

OTHER PUBLICATIONS

European Search Report for EP Patent Application No. 11008013, dated Jan. 20, 2012.

\* cited by examiner

*Primary Examiner* — Thomas McEvoy
(74) *Attorney, Agent, or Firm* — Bachman & LaPointe, P.C.

(57) ABSTRACT

A medical instrument for cutting biological tissue, a cutting module having a blade, wherein the cutting module is inserted into a hand-held module, the cutting module is detachably fixed in the hand-held module.

14 Claims, 5 Drawing Sheets

MEDICAL INSTRUMENT

BACKGROUND OF THE INVENTION

The invention relates to a medical instrument for cutting biological, more particularly human, tissue by means of a cutting module with a blade, which cutting module is inserted into a hand-held module.

Although the present case in particular relates to a specific medical instrument, which is also known by the technical term of "morcellator", the invention should not be restricted thereto. The invention is to be applied wherever a rotating cutting module, which in particular is embodied as a cutting tube, carries out an action in the body of a living being. These days such medical instruments are primarily used in endoscopic interventions. They serve to remove relatively large proportions of tissue.

The morcellator in particular has a cutting tube as a cutting module, which cutting tube has a blade at the distal end. By way of example, this cutting tube is introduced into the body through an endoscope and then set into rotational motion. As a result of this, the blade removes tissue components, which are then taken out of the body through the cutting tube itself. To this end, the tissue part can be suctioned away or else be removed by a further medical instrument, the latter then for example being routed into the cutting tube through a valve module and being routed through said cutting tube. By way of example, such a medical instrument is described in DE 103 58 279 A1.

It is an object of the present invention to design the above-described medical instrument in a more manageable and flexible fashion.

SUMMARY OF THE INVENTION

The object is achieved by virtue of the fact that the cutting module is detachably fixed in the hand-held module.

This means that, for example, there can always be the same hand-held module, while the cutting module is replaced. The cutting module can be replaced by a similar cutting module in the case of wear-and-tear or contamination, but the use of differently designed cutting modules for different medical actions is also feasible.

In a preferred exemplary embodiment of the invention, the cutting module is embodied as a hollow cutting tube, which is connected to the hand-held module such that it can rotate about its own axis. In this case, the medical instrument forms a morcellator.

The detachable connection between cutting module and hand-held module should preferably be embodied as a connection by means of a catch mechanism. This means that the cutting tube is simply inserted into the hand-held module and connected by a catch or snap-in mechanism. The cutting module can likewise be removed from the hand-held module by pulling the cutting module and/or the hand-held module.

A connection by means of a catch mechanism is brought about by virtue of the fact that a catch, preferably embodied as a catch spring, is arranged on an element, which catch interacts with a corresponding catching lug in the hand-held module. Here, the catch or catch spring itself can be formed out of the cutting tube and is preferably designed to be inherently resilient such that it gives way to the inside when the cutting module is inserted into the hand-held module and thereafter snaps behind the catching lug. It likewise gives way to the inside when the cutting module is pulled out of the hand-held module, and drives over the catching lug. Here, the catching lug may be provided in an annular fashion as inner ring in a receptacle element in the hand-held module however, other options are also feasible.

Moreover, an outer gear ring should be assigned to the cutting module, which outer gear ring interacts with an inner gear ring in the hand-held module. This inner gear ring is connected via a ring bevel gear to a bevel drive gear, which in turn is preferably placed on a rotational shaft of a rotor. This is how the rotational motion of the rotational shaft is transmitted to the cutting module.

For the support during the rotation, preferably two spaced apart sliding bearing rings are placed on the cutting module, which sliding bearing rings rotate in corresponding sliding bearings in the receptacle element in the hand-held module.

For the last-described arrangement, independent protection is also desired since provision is made for the cutting module with the sliding rings to be mounted in the sliding bearings with at least 0.2 Nm, but with at most 5 Nm. The sliding rings are pressed onto the cutting module by force fit; furthermore, the cutting module is intended to have a multi-part design, particularly in the proximal region which is inserted into the hand-held module.

A further idea of the present invention relates to the embodiment of the distal end of the cutting module. Here, provision should be made for one section made of hardened flat-bar steel, which section also forms the blade. Here, this cutting element, which is formed from flat-bar steel, may, in one option, be arranged such that it radially encloses the cutting module or it is inserted into the cutting module. Furthermore, it can also be placed directly against the cutting module in the manner of a butt joint.

A valve unit is preferably inserted into the hand-held module at the end opposite the cutting module. Said valve unit can be connected to the hand-held module by means of a bayonet-like connection. Situated within the valve unit is a valve, which allows the insertion of a further medical instrument, but surrounds this instrument in a manner that is as airtight as possible.

BRIEF DESCRIPTION OF THE DRAWINGS

Further advantages, features and details of the invention emerge from the following description of preferred exemplary embodiments and on the basis of the drawing, in which.

DETAILED DESCRIPTION

Figure 1:
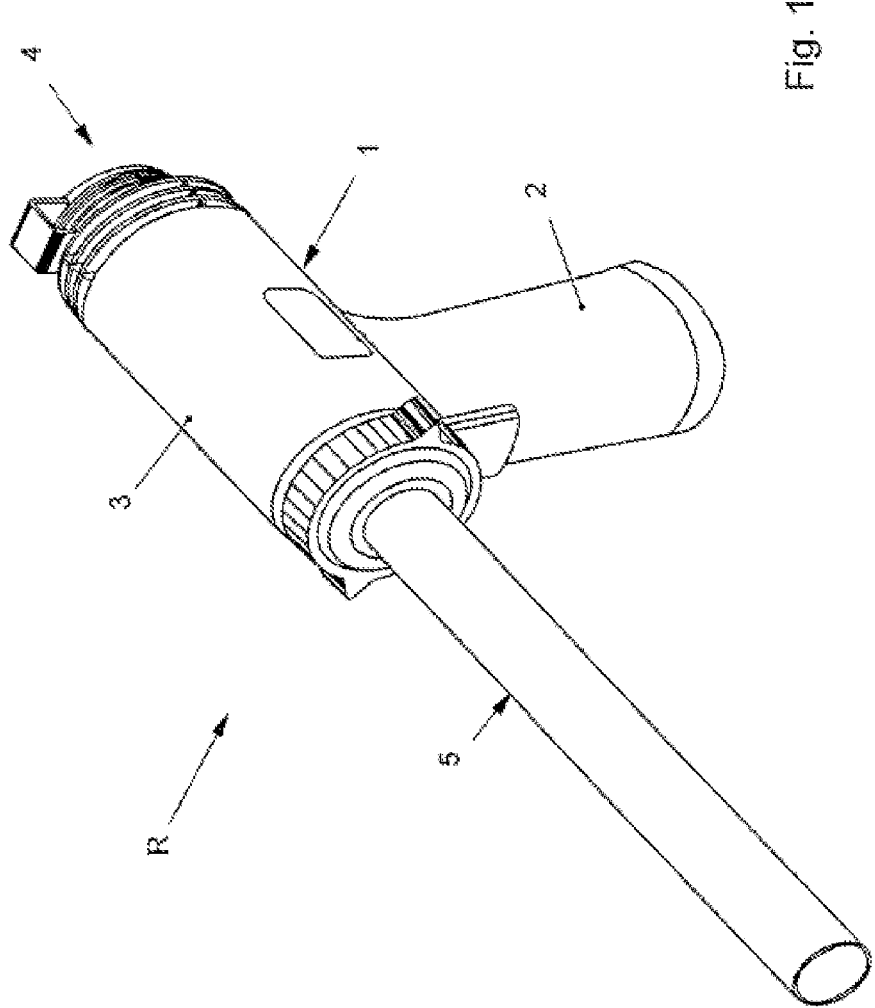
FIG. 1 shows a perspective view of a medical instrument according to the invention for cutting human tissue.
Figure 2:
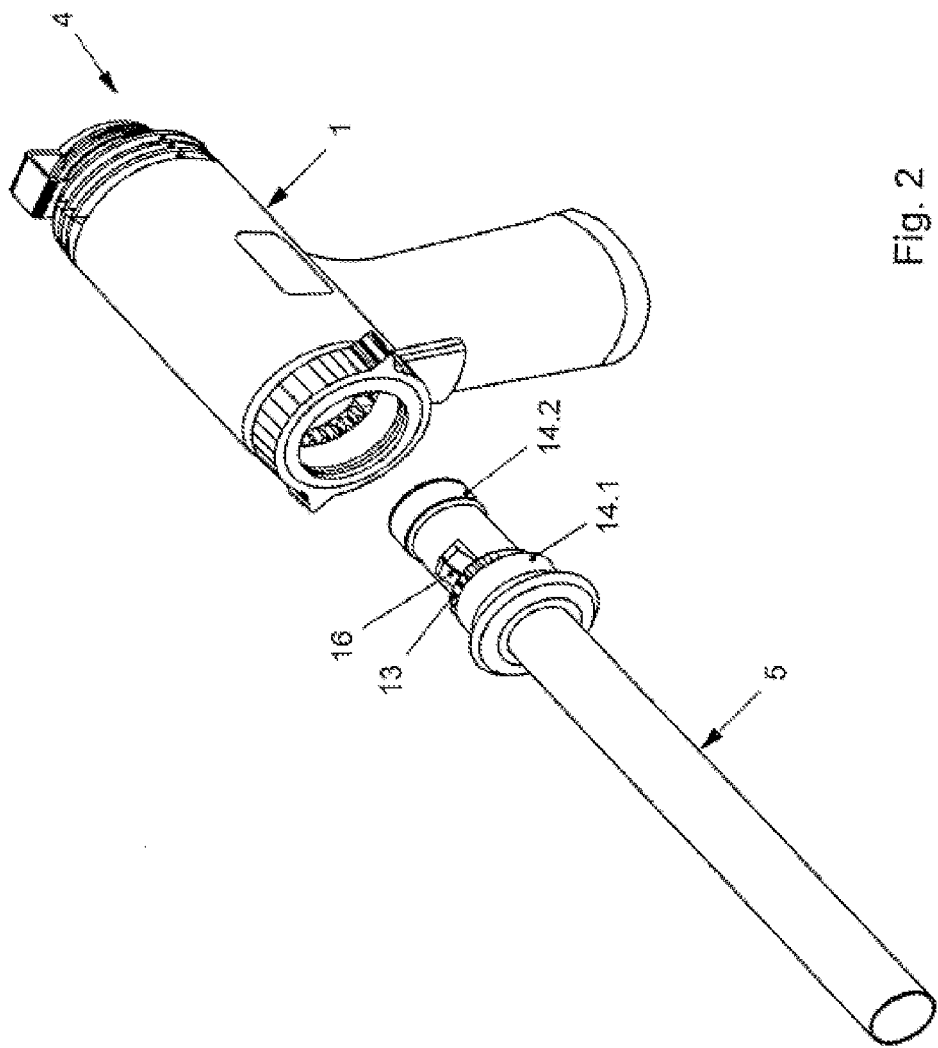
FIG. 2 shows a perspective view of the medical instrument as per FIG. 1, partly in an exploded view.
Figure 3:
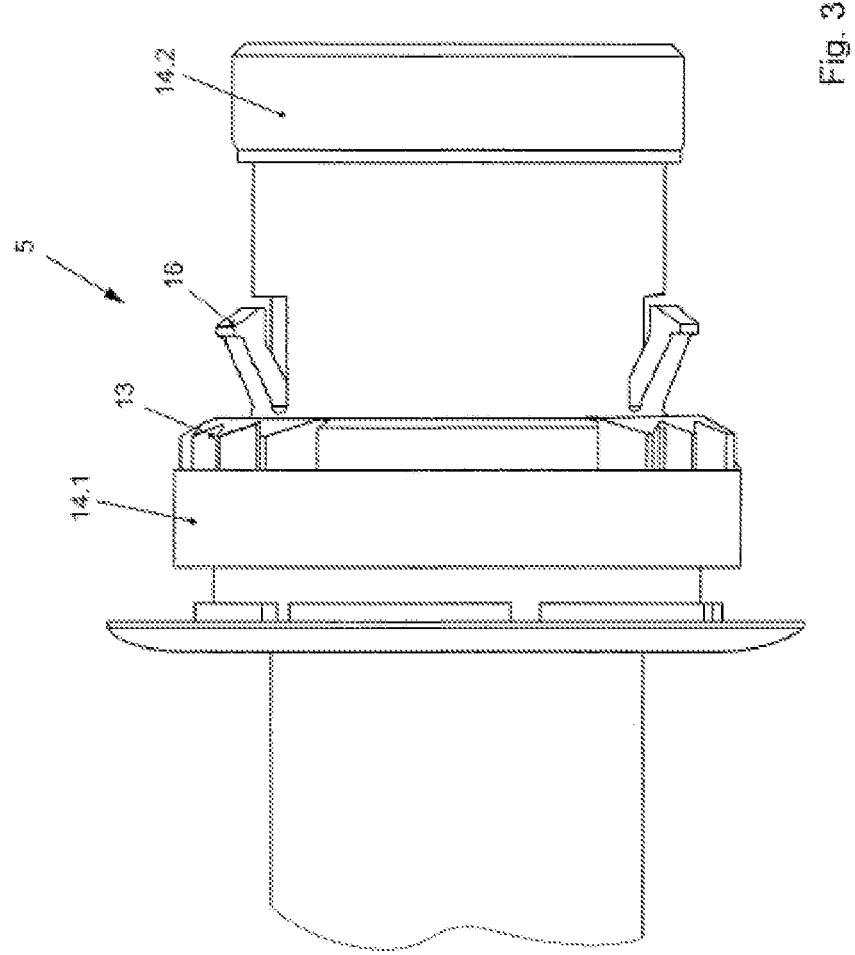
FIG. 3 shows a plan view of an insertion region of a cutting tube according to the invention.

As per FIG. 1, a medical instrument R according to the invention has a hand-held module 1, which consists of a grip part 2 and a guidance part 3. A valve module 4 is inserted into one open end of the guidance part 3 and a cutting module 5 is inserted into the other open end. Situated in the grip part 2 is a motor (shown in FIG. 4), with a bevel drive gear 7 being placed on the rotational shaft 6 thereof. This bevel drive gear 7 interacts with a ring bevel gear 8, which surrounds a receptacle element 9 in the guidance part of the hand-held module 1, with an annularly designed catching lug 10 engaging into a corresponding annular groove 11 in the receptacle element 9. This annular groove 11 in turn forms an annular catching lug into the interior of the receptacle element 9.

Figure 4:
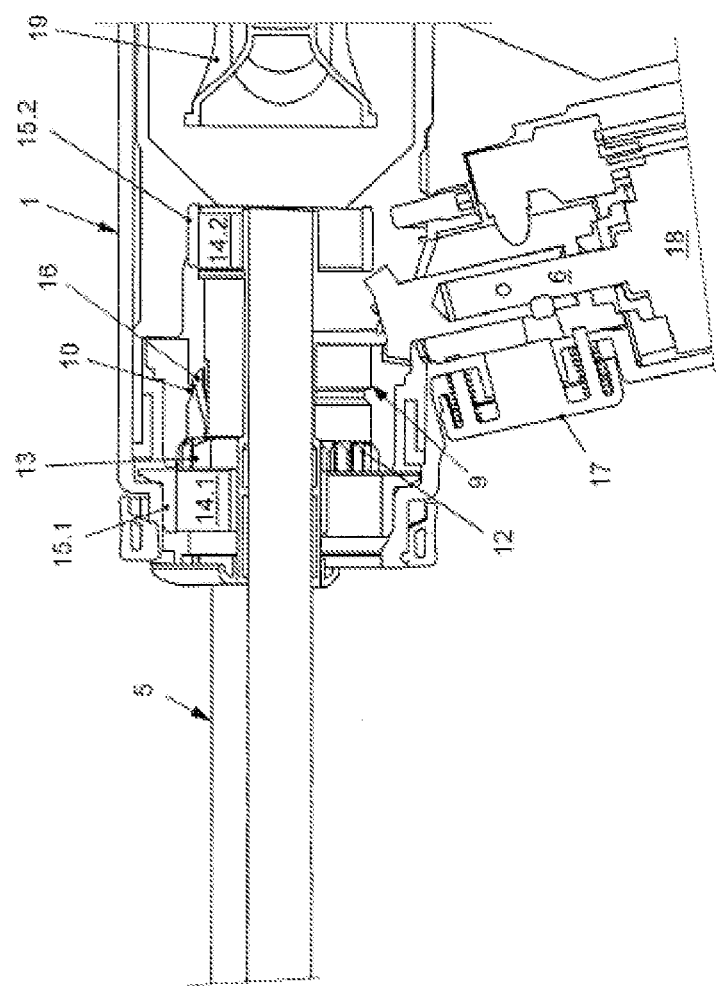
FIG. 4 shows a partly illustrated longitudinal section through a hand-held module with an inserted cutting tube.

In the usage position as per FIG. 4, the ring bevel gear 8 overlaps an outer gear ring 13 with an inner gear ring 12, which outer gear ring 13 is placed on the cutting module 5 embodied as a cutting tube. This transmits rotational motion of the bevel drive gear 7 via the ring bevel gear 8 onto the outer gear ring 13 and the cutting module 5 is rotated about its longitudinal axis.

In order to support the cutting module 5 during the rotation about its longitudinal axis, two spaced apart sliding rings 14.1 and 14.2 are placed on the cutting module 5 and these sliding rings in turn rotate in a front sliding bearing 15.1 and a rear sliding bearing 15.2.

Moreover, it is possible to identify that the cutting module 5 is inserted in a detachable fashion into the hand-held module 1 or the receptacle element 9 by means of a connection with a catch mechanism. To this end, catch springs 16 project from the cutting module 5 between the rear sliding bearing 15.2 and the outer gear ring 13, and said catch springs engage behind the catch groove 11 that projects inwards as a catch lug in the assembled state.

The present invention functions as follows:

After inserting the cutting module 5 into e.g. a human body for removing tissue, for example through a trocar, the motor 18 or the rotational shaft 6 thereof is set into rotational motion via a pushbutton 17. In the process, the bevel drive gear 7 also rotates and drives the cutting module 5, or sets the latter into rotational motion, via the ring bevel gear 8, the inner gear ring 12 thereof and the outer gear ring 13. In the process, the sliding rings 14.1 and 14.2 rotate in the corresponding sliding bearings 15.1 and 15.2. The catch springs 16 engage behind the annular catching lugs projecting into the interior of the receptacle element 9.

Should it be deemed necessary, a further surgical instrument can be inserted through a corresponding valve 19 in the valve module 4, which surgical instrument can then also be routed through the cutting module 5 to the distal end thereof.

Figure 5:
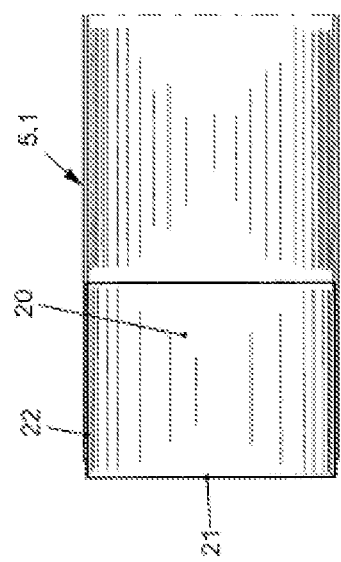
FIG. 5 shows a partly illustrated longitudinal section through an exemplary embodiment of a distal end of a cutting tube.

According to the invention, a blade or a cutting element 20 with a blade 21 is situated at the distal end of the cutting module 5. Within the scope of the present invention, this cutting element 20 is made of spring steel and rolled together to form a sleeve. As per FIG. 5, an inner groove 22 is formed in a corresponding cutting module 5.1 for holding this cutting element 20 and so the cutting element 20 is inserted into the interior of the cutting module 5.1.

Figure 6:
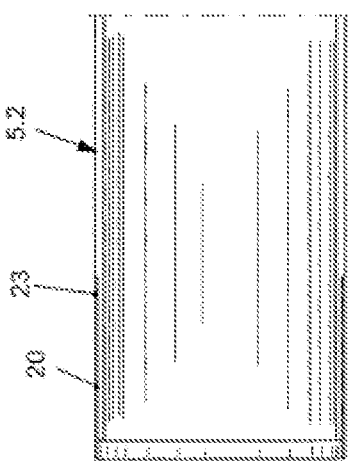
FIG. 6 shows a partly illustrated longitudinal section through a further exemplary embodiment of a distal end region of a cutting tube.

As per FIG. 6, a cutting module 5.2 has an outer groove 23 into which the cutting element 20 is inserted. That is to say in this case the cutting element 20 surrounds the distal end of the cutting module 5.2.

Figure 7:
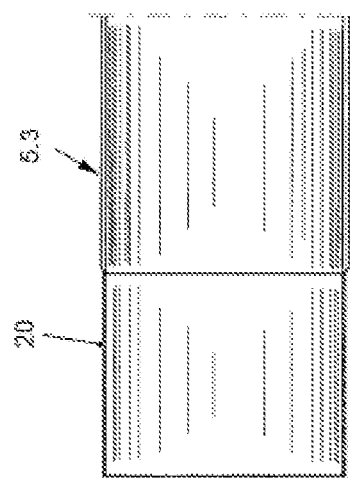
FIG. 7 shows a partly illustrated longitudinal section through a further exemplary embodiment of a distal end region of a cutting tube.

As per FIG. 7, the cutting element 20 is placed against a cutting module 5.3 in the form of a butt joint or is butt welded to this cutting module 5.3.

The invention claimed is:

1. Medical instrument for cutting biological tissue comprising a cutting module with a blade, the cutting module is inserted into a hand-held module and is connected to the hand-held module by a catch mechanism, the catch mechanism comprises at least one catch assigned to the cutting module which interacts with a catching lug in the hand-held module, the catching lug is formed as an inner ring in a receptacle element, a gear ring is arranged on the cutting module and interacts with an inner gear ring in the hand-held module, the inner gear ring is situated on the receptacle element, and the cutting module is detachably fixed in the hand-held module.

2. Medical instrument according to claim 1, wherein the cutting module comprises a hollow cutting tube connected to the hand-held module such that it can rotate about a rotational axis of the cutting module.

3. Medical instrument according to claim 1, wherein the at least one catch is formed out of the hollow cutting tube and is inherently resilient.

4. Medical instrument according to claim 1, wherein a bevel gear is arranged on the receptacle element and interacts with a further bevel gear that is on a rotational shaft of a motor.

5. Medical instrument according to claim 1, wherein two spaced apart sliding bearing rings are located on the cutting module and interact with two sliding bearings in the hand-held module.

6. Medical instrument according to claim 1, wherein the hand-held module includes at least one sliding bearing which is arranged on sliding rings on the cutting module having a defined moment of friction of between 0.2 Nm and 5 Nm.

7. Medical instrument according to claim 6, wherein the sliding bearing rings are pressed onto the cutting module by force fit.

8. Medical instrument according to claim 7, wherein a receptacle element in the hand-held module is connected to the cutting module by a catch mechanism.

9. Medical instrument according to claim 8, wherein the cutting module is made of plastic that autodestructs upon steam sterilization.

10. Medical instrument according to claim 6, wherein a valve module is connected by a bayonet connection to the hand-held module at an end of the cutting module.

11. Medical instrument according to claim 1, wherein the blade, which comprises hardened flat-bar steel, is arranged distally on the cutting module.

12. Medical instrument according to claim 11, wherein the cutting module comprises a cutting tube, wherein the blade is arranged distally on the cutting tube in a radially enclosing or surrounding fashion.

13. Medical instrument according to claim 11, wherein the blade is placed against the cutting module in the manner of a butt joint.

14. Medical instrument according to claim 11, wherein the blade is inserted into a groove formed on the distal end of the cutting module.

\* \* \* \* \*